United States Patent
Watson et al.

(10) Patent No.: US 10,288,554 B2
(45) Date of Patent: May 14, 2019

(54) MOISTURE DETECTING BLEEDER MATERIALS

(71) Applicant: THE BOEING COMPANY, Chicago, IL (US)

(72) Inventors: Megan N. Watson, Summerville, SC (US); Justin H. Register, Charleston, SC (US); Meredith M. Bird, Mt. Pleasant, SC (US)

(73) Assignee: THE BOEING COMPANY, Chicago, IL (US)

( * ) Notice: Subject to any disclaimer, the term of this patent is extended or adjusted under 35 U.S.C. 154(b) by 206 days.

(21) Appl. No.: 15/008,302

(22) Filed: Jan. 27, 2016

(65) Prior Publication Data
US 2017/0212038 A1   Jul. 27, 2017

(51) Int. Cl.
| | |
|---|---|
| *B29C 65/00* | (2006.01) |
| *B29C 65/02* | (2006.01) |
| *B32B 37/00* | (2006.01) |
| *B32B 38/00* | (2006.01) |
| *B29C 73/00* | (2006.01) |

(Continued)

(52) U.S. Cl.
CPC ............ *G01N 21/29* (2013.01); *B29C 73/10* (2013.01); *G01N 21/84* (2013.01); *B29C 65/4835* (2013.01); *B29C 66/0242* (2013.01); *B29C 66/301* (2013.01); *B29C 66/721* (2013.01); *B29C 66/953* (2013.01); *B32B 27/04* (2013.01); *B32B 37/1207* (2013.01); *B32B 37/18* (2013.01); *B32B 2038/166* (2013.01)

(58) Field of Classification Search
CPC ...... G01N 31/222; G01N 21/81; B32B 27/04; B32B 27/12; B32B 37/0007; B32B 37/003; B32B 37/1207; B32B 37/18; B32B 37/182; B32B 38/00; B32B 2038/166; B29C 73/10; B29C 65/48; B29C 65/4835; B29C 66/02; B29C 66/0224; B29C 66/0242; B29C 66/301; B29C 66/721; B29C 66/953; B29C 66/9532; B29C 66/9534
USPC ......... 156/60, 64, 90, 94, 98, 153, 250, 256, 156/257, 258, 285, 286, 289, 293, 307.1, 156/307.4; 73/73, 29.04; 116/206
See application file for complete search history.

(56) References Cited

U.S. PATENT DOCUMENTS

| | | |
|---|---|---|
| 3,173,880 A | 3/1965 | Pappas et al. |
| 4,909,179 A | 3/1990 | McBride |

(Continued)

FOREIGN PATENT DOCUMENTS

| | | |
|---|---|---|
| EP | 1818091 A1 | 8/2007 |
| EP | 1849708 A1 | 10/2007 |
| EP | 2671708 A1 | 12/2013 |

OTHER PUBLICATIONS

Extended European Search Report, Application No. 17153010, dated Jun. 30, 2017, 7 pages.

*Primary Examiner* — Philip C Tucker
*Assistant Examiner* — Brian R Slawski
(74) *Attorney, Agent, or Firm* — Toler Law Group, P.C.

(57) ABSTRACT

A moisture detecting bleeder material includes a fiberglass material and a moisture absorption indicator material. The moisture absorption indicator material is a component of the fiberglass material and undergoes a color change from a first color to a second color when exposed to moisture. The color change may be thermally irreversible below a threshold temperature (e.g., below a temperature of 450° F.).

15 Claims, 4 Drawing Sheets

(51) Int. Cl.
    *B32B 43/00*     (2006.01)
    *G01N 5/02*     (2006.01)
    *G01N 25/56*     (2006.01)
    *G01N 7/00*     (2006.01)
    *G01N 9/36*     (2006.01)
    *G01N 19/10*     (2006.01)
    *G01N 21/29*     (2006.01)
    *G01N 21/84*     (2006.01)
    *B29C 73/10*     (2006.01)
    *B32B 38/16*     (2006.01)
    *B32B 27/04*     (2006.01)
    *B32B 37/12*     (2006.01)
    *B29C 65/48*     (2006.01)
    *B32B 37/18*     (2006.01)

(56) References Cited

U.S. PATENT DOCUMENTS

| | | | |
|---|---|---|---|
| 2011/0132523 A1 | 6/2011 | Evens et al. | |
| 2012/0061261 A1* | 3/2012 | Hsu | B01D 53/261 |
| | | | 206/204 |
| 2013/0056131 A1* | 3/2013 | Whitworth | B29C 37/006 |
| | | | 156/64 |
| 2013/0330832 A1* | 12/2013 | Seegel | B29C 70/443 |
| | | | 436/172 |
| 2014/0000788 A1* | 1/2014 | Evens | B29C 73/10 |
| | | | 156/94 |

* cited by examiner

MOISTURE DETECTING BLEEDER MATERIALS

FIELD OF THE DISCLOSURE

The present disclosure is generally related to moisture detecting bleeder materials.

BACKGROUND

During repair of a composite part, the presence of moisture may be associated with various problems, such as inhibiting adhesion of repair materials to the composite part. A repair area is typically dried before the repair, and steps are taken to prevent moisture ingression. After drying, it may be difficult to detect moisture ingress. As a result, if procedures were followed and the repair appears to be satisfactory, an assumption is typically made that there was no moisture ingression during the repair process.

SUMMARY

In a particular embodiment, a method includes applying a plurality of layers to a composite repair area. The plurality of layers includes a moisture detecting bleeder material that includes a moisture absorption indicator material. A color change of the moisture absorption indicator material from a first color to a second color is indicative of moisture absorption by the moisture absorption indicator material. The method includes applying a bagging film to the composite repair area. The bagging film includes a fluid interface, and the method includes performing a moisture removal operation that includes applying a vacuum (e.g., a pressure that is less than an ambient pressure) to the fluid interface. The method also includes removing the bagging film to expose the moisture detecting bleeder material. The method further includes evaluating the exposed moisture detecting bleeder material to determine whether the color change occurred.

In another particular embodiment, a method includes applying a composite repair formulation to a composite repair area. After applying the composite repair formulation, the method includes applying a plurality of layers to the composite repair area. The plurality of layers includes a moisture detecting bleeder material that includes a moisture absorption indicator material. A color change of the moisture absorption indicator material from a first color to a second color is indicative of moisture absorption by the moisture absorption indicator material. The method also includes applying a bagging film to the composite repair area, performing a curing operation that includes heating the composite repair formulation, and removing the bagging film to expose the moisture detecting bleeder material. The method further includes evaluating the exposed moisture detecting bleeder material to determine whether the color change occurred.

In another particular embodiment, a moisture detecting bleeder material includes a fiberglass material and a moisture absorption indicator material. The moisture absorption indicator material undergoes a color change from a first color to a second color when exposed to moisture. The color change is thermally irreversible below a temperature of 450° F.

The features, functions, and advantages that have been described can be achieved independently in various embodiments or may be combined in other embodiments, further details of which are disclosed with reference to the following description and drawings.

DETAILED DESCRIPTION

The present disclosure describes moisture detecting bleeder materials (e.g., bleeder cloths including woven fibers or bleeder mats including non-woven fibers) that may be utilized to determine whether moisture was absorbed during one or more operations associated with repair of a composite part. For example, the moisture detecting bleeder materials of the present disclosure may be used to determine whether a moisture removal operation was satisfactory and/or whether a curing operation was satisfactory. The moisture detecting bleeder materials of the present disclosure include a moisture absorbing indicator material. A color change of the moisture absorption indicator material from a first color (e.g., a white color) to a second color (e.g., a non-white color, such as blue) is indicative of moisture absorption by the moisture absorption indicator material.

Figure 1:
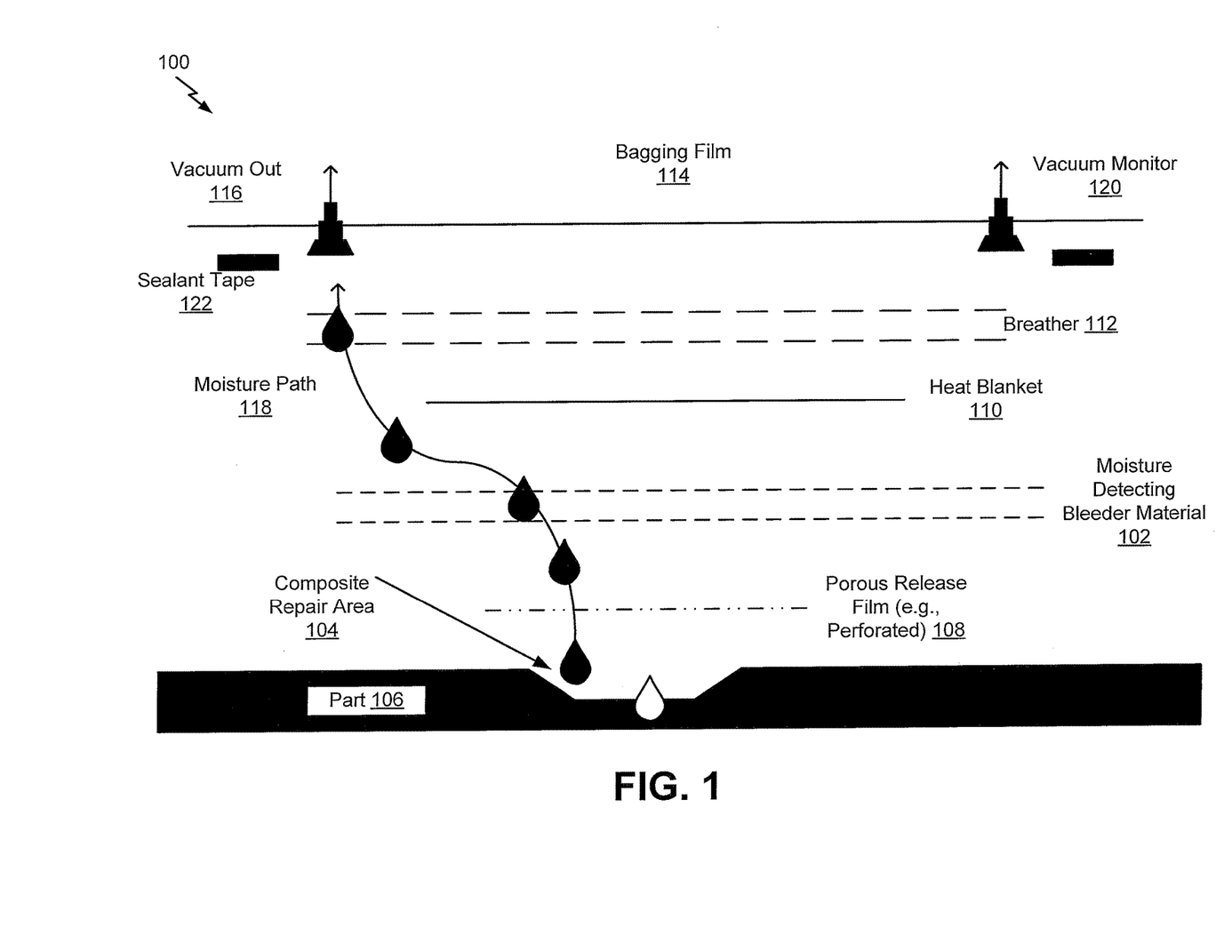
FIG. 1 is a diagram illustrating a moisture removal operation (associated with a composite repair operation) that includes application of a moisture detecting bleeder material to a composite repair area, according to one embodiment.

In some cases, the moisture detecting bleeder materials of the present disclosure may be utilized to evaluate an effectiveness of a moisture removal operation (associated with a composite repair operation), as illustrated and further described herein with respect to FIG. 1. In other cases, moisture detecting bleeder materials of the present disclosure may be utilized to evaluate an effectiveness of a curing operation (associated with the composite repair operation), as illustrated and further described herein with respect to FIG. 2. In the case of the moisture removal operation, the absorption of moisture by the moisture absorption indicator material is indicative of the satisfactory removal of moisture prior to performing one or more subsequent composite repair operations. In the case of the curing operation, the absorption of moisture by the moisture absorption indicator material is indicative of the presence of moisture resulting from moisture ingression through the composite part and/or humidity from a vacuum bagging leak. As the presence of moisture during the curing operation may result in an unsatisfactory repair (e.g., associated with porosity in a laminate patch or a bonded adhesive joint), a color change may be indicative of an unsatisfactory composite repair operation.

Referring to FIG. 1, a diagram 100 illustrates a particular embodiment of a moisture removal operation (associated with a composite repair operation) that includes application of a moisture detecting bleeder material 102 to a composite repair area 104 (of a composite part 106). The moisture detecting bleeder material 102 includes a moisture absorption indicator material, and a color change of the moisture absorption indicator material from a first color (e.g., a white color) to a second color (e.g., a non-white color, such as a blue color) is indicative of moisture absorption by the moisture absorption indicator material. For example, the moisture detecting bleeder material 102 may include a fiberglass material, and the moisture absorption indicator material may be a component of the fiberglass material (e.g., dispersed in the fiberglass material). As described further herein, the color change may be indicative of a satisfactory moisture removal operation.

In the particular embodiment illustrated in FIG. 1, a plurality of layers are applied to the composite repair area 104. In the example of FIG. 1, the plurality of layers includes a porous release film layer 108 (e.g., a perforated release film) between the moisture detecting bleeder material 102 and the composite repair area 104. The plurality of layers also includes a heat blanket layer 110 overlying the moisture detecting bleeder material 102 and a breather layer 112 overlying the heat blanket layer 110. In other cases, the plurality of layers may include fewer layers or more layers. While FIG. 1 illustrates an example in which a heat source for the moisture removal operation is the heat blanket layer 110, in other cases, the heat source may be an oven or an autoclave. In such cases, the heat blanket layer 110 may be omitted from the plurality of layers. A bagging film 114 that includes at least one fluid interface may be applied to the composite repair area 104. In the example of FIG. 1, the bagging film 114 includes a fluid interface 116 (identified as "Vacuum Out" in FIG. 1) that enables the application of a vacuum (e.g., a pressure that is less than an ambient pressure) to the composite repair area 104, providing a moisture path 118 for removal of moisture from the composite repair area 104. In the particular embodiment illustrated in FIG. 1, a second fluid interface 120 (identified as "Vacuum Monitor" in FIG. 1) may enable monitoring of the vacuum during the moisture removal operation.

FIG. 1 illustrates a particular example in which sealant tape 122 is used to secure the bagging film 114 (as well as the plurality of layers below the bagging film 114) over the composite repair area 104. In other cases, alternative and/or additional sealing methods may be employed in order to seal the bagging film 114 to the composite part 106 to enable the application of the vacuum to the composite repair area 104 for moisture removal. After application of the multiple layers to the composite repair area 104, a moisture removal operation may be performed that includes applying a vacuum to the fluid interface 116. After performing the moisture removal operation, the bagging film 114 may be removed to expose the moisture detecting bleeder material 102. The exposed moisture detecting bleeder material 102 may be evaluated to determine whether the color change occurred. When the color change occurred, the moisture removal operation may be considered a satisfactory moisture removal operation because the color change indicates that moisture passed through the moisture detecting bleeder material 102. As illustrated and further described herein with respect to FIG. 2, a curing operation may be performed after determining that the moisture removal operation was successful based on the color change. Alternatively, a lack of color change may be associated with an unsatisfactory moisture removal operation because the lack of color change indicates that moisture did not pass through the moisture detecting bleeder material 102. In this case, a second or additional moisture removal operation may be performed after determining that the color change did not occur.

In a particular embodiment, the color change of the moisture absorption indicator material of the moisture detecting bleeder cloth layer 102 is thermally irreversible within a temperature range associated with the process conditions of the moisture removal operation. For example, the color change may be thermally irreversible below a temperature of 450° F. The moisture absorption indicator material may include a metal halide material, such as chloride material, a bromide material, or a combination thereof (e.g., where the metal includes nickel, cobalt, or a combination thereof). Illustrative, non-limiting examples include Nickel II Bromide, Cobalt II Chloride, Cobalt II Bromide, among other alternatives (or combinations thereof). In some cases, the metal halide material(s) may be a component of a silica gel (e.g., dispersed in an activated silica gel).

Figure 2:
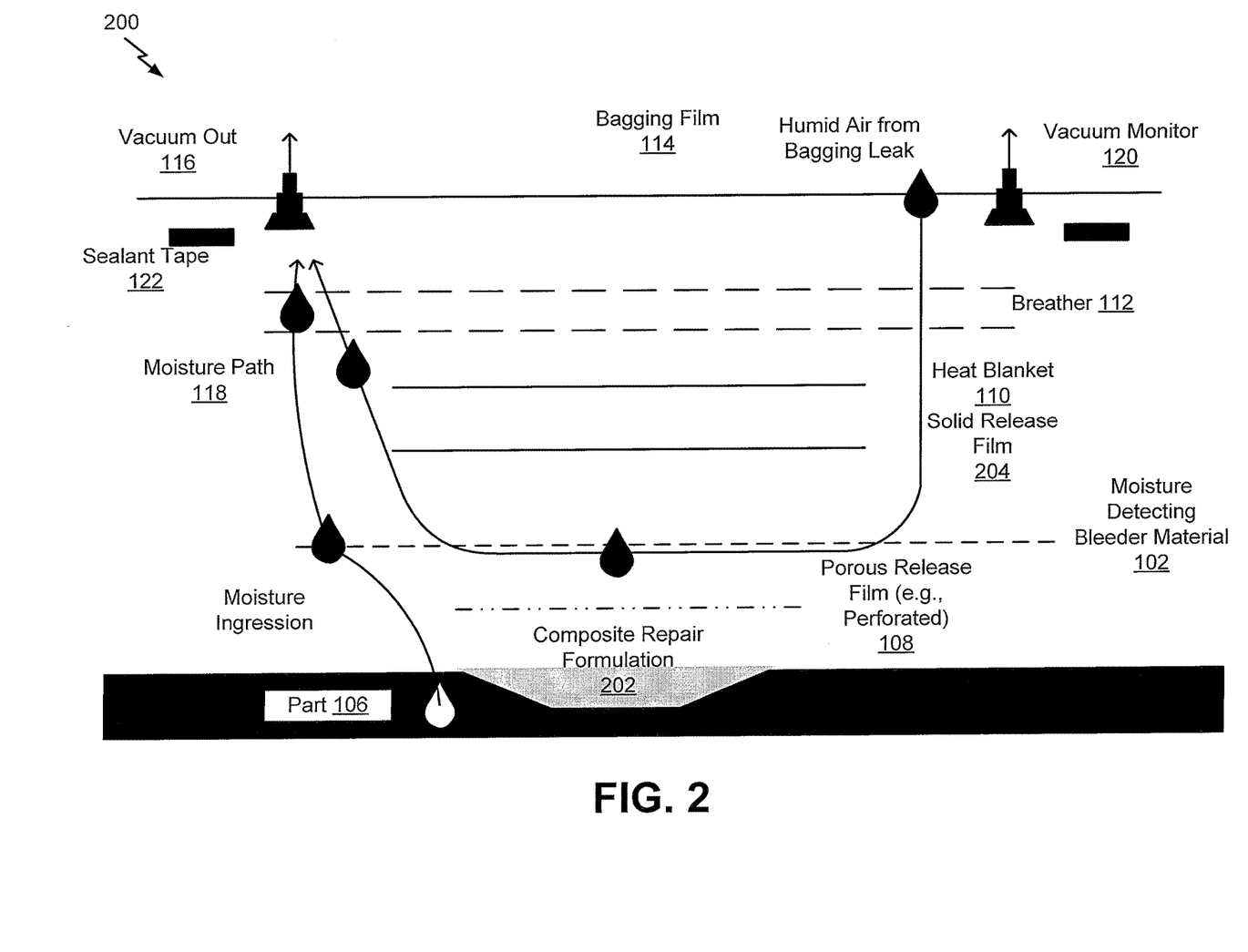
FIG. 2 is a diagram illustrating a curing operation (associated with a composite repair operation) that includes application of a moisture detecting bleeder material to a composite repair area, according to one embodiment.

Thus, FIG. 1 illustrates an example of a moisture removal operation that may be performed prior to a curing operation of a composite repair operation (as described further herein with respect to FIG. 2). The moisture removal operation includes the use of a moisture detecting bleeder material that includes a moisture absorption indicator material that changes color from a first color to a second color when exposed to moisture. After the moisture removal operation, the moisture detecting bleeder material may be evaluated in order to determine whether the moisture absorption indicator material changed color as a result of exposure to moisture. A color change of the moisture absorption indicator material from the first color to the second color may be indicative of moisture absorption during the moisture removal operation, representing a satisfactory moisture removal operation, while the absence of a color change may be indicative of an unsatisfactory moisture removal operation.

Referring to FIG. 2, a diagram 200 illustrates a particular embodiment of a curing operation (associated with a composite repair operation) that includes application of the moisture detecting bleeder material 102 to the composite repair area 104 (of the composite part 106). FIG. 2 illustrates that a composite repair formulation 202 (e.g., a pre-impregnated material, also referred to as a "prepreg material") is applied to the composite repair area 104 prior to applying the other layers of a composite repair layup. The curing operation may be performed after a satisfactory moisture removal operation, as described herein with respect to FIG. 1. Alternatively, the moisture detecting bleeder material 102 may be utilized for only the moisture removal operation or for only the curing operation. As in the example of FIG. 1, the moisture detecting bleeder material 102 of FIG. 2 includes the moisture absorption indicator material that changes color from the first color to the second color when exposed to moisture. After the curing operation, the moisture detecting bleeder material 102 may be evaluated in order to determine whether the moisture absorption indicator material changed color as a result of exposure to moisture. A color change from the first color to the second color is indicative of the presence of moisture during the curing operation, representing an unsatisfactory curing operation, while the absence of a color change is indicative of a satisfactory curing operation.

The composite repair formulation 202 may include one or more volatile components. During the curing operation, heat may be applied to the composite repair formulation 202 (e.g., via the heat blanket layer 110 or via another heat source, such as an oven or an autoclave), and the volatile component(s) may be removed via application of a vacuum (e.g., a pressure that is less than an ambient pressure) via the fluid interface 116. In some cases, exposure of the moisture detecting bleeder material 102 to the volatile component(s) may not result in the color change from the first color to the second color. In a particular embodiment, the color change of the moisture absorption indicator material is thermally irreversible within a temperature range associated with the process conditions of the curing operation. For example, the color change may be thermally irreversible below a temperature of 450° F. that may represent a maximum temperature that results from application of heat to the composite repair formulation 202. As an example, the moisture absorption indicator material may include a metal halide material, such as chloride material, a bromide material, or a combination thereof (e.g., where the metal includes nickel, cobalt, or a combination thereof). Illustrative, non-limiting examples include Nickel II Bromide, Cobalt II Chloride, Cobalt II Bromide, among other alternatives (or combinations thereof). In some cases, the metal halide material(s) may be a component of a silica gel (e.g., dispersed in an activated silica gel).

FIG. 2 illustrates that a plurality of layers may be applied after the composite repair formulation 202 has been applied to the composite repair area 104. In the example of FIG. 2, the plurality of layers includes the porous release film layer 108 (e.g., a perforated release film) between the moisture detecting bleeder material 102 and the composite repair area 104 (that includes the composite repair formulation 202). The plurality of layers also includes a solid release film layer 204 overlying the moisture detecting bleeder material 102, the heat blanket layer 110 overlying the solid release film layer 204, and the breather layer 112 overlying the heat blanket layer 110. In other cases, the plurality of layers may include fewer layers or more layers. While FIG. 2 illustrates an example in which a heat source for the curing operation is the heat blanket layer 110, in other cases, the heat source may be an oven or an autoclave. In such cases, the heat blanket layer 110 may be omitted from the plurality of layers. The bagging film 114 (that includes the fluid interface 116) may be applied to the composite repair area 104 after application of the plurality of layers, and the bagging film 114 may seal the composite repair area 104 (e.g., using the sealant tape 122).

After application of the multiple layers to the composite repair area 104, a curing operation may be performed that includes applying a vacuum to the fluid interface 116 and applying heat (e.g., via the heat blanket layer 110 or via another heat source). After performing the curing operation, the bagging film 114 may be removed to expose the moisture detecting bleeder material 102. The exposed moisture detecting bleeder material 102 may be evaluated to determine whether the color change occurred. A color change may be indicative of moisture ingression from one or more locations during the curing operation (shown in FIG. 2 as "Moisture Ingression" and "Humid Air from Bagging Leak") or ineffective drying before the curing operation. Accordingly, the color change may indicate that the curing operation was an unsatisfactory curing operation. Alternatively, a lack of color change may be associated with a satisfactory curing operation.

Thus, FIG. 2 illustrates an example of a curing operation associated with a composite repair operation. The curing operation includes the use of a moisture detecting bleeder material that includes a moisture absorption indicator material that changes color from a first color to a second color when exposed to moisture. After the curing operation, the moisture detecting bleeder material may be evaluated in order to determine whether the moisture absorption indicator material changed color. The color change may be thermally irreversible at a temperature associated with the curing operation. Unlike dessicant canisters that experience color reversion under high temperature conditions, the moisture absorption indicator material of the present disclosure may retain the color change in order to determine whether moisture was present during the curing operation. A color change from the first color to the second color is indicative of moisture incursion during the curing operation, representing an unsatisfactory curing operation, while the absence of a color change is indicative of a satisfactory curing operation.

Figure 3:
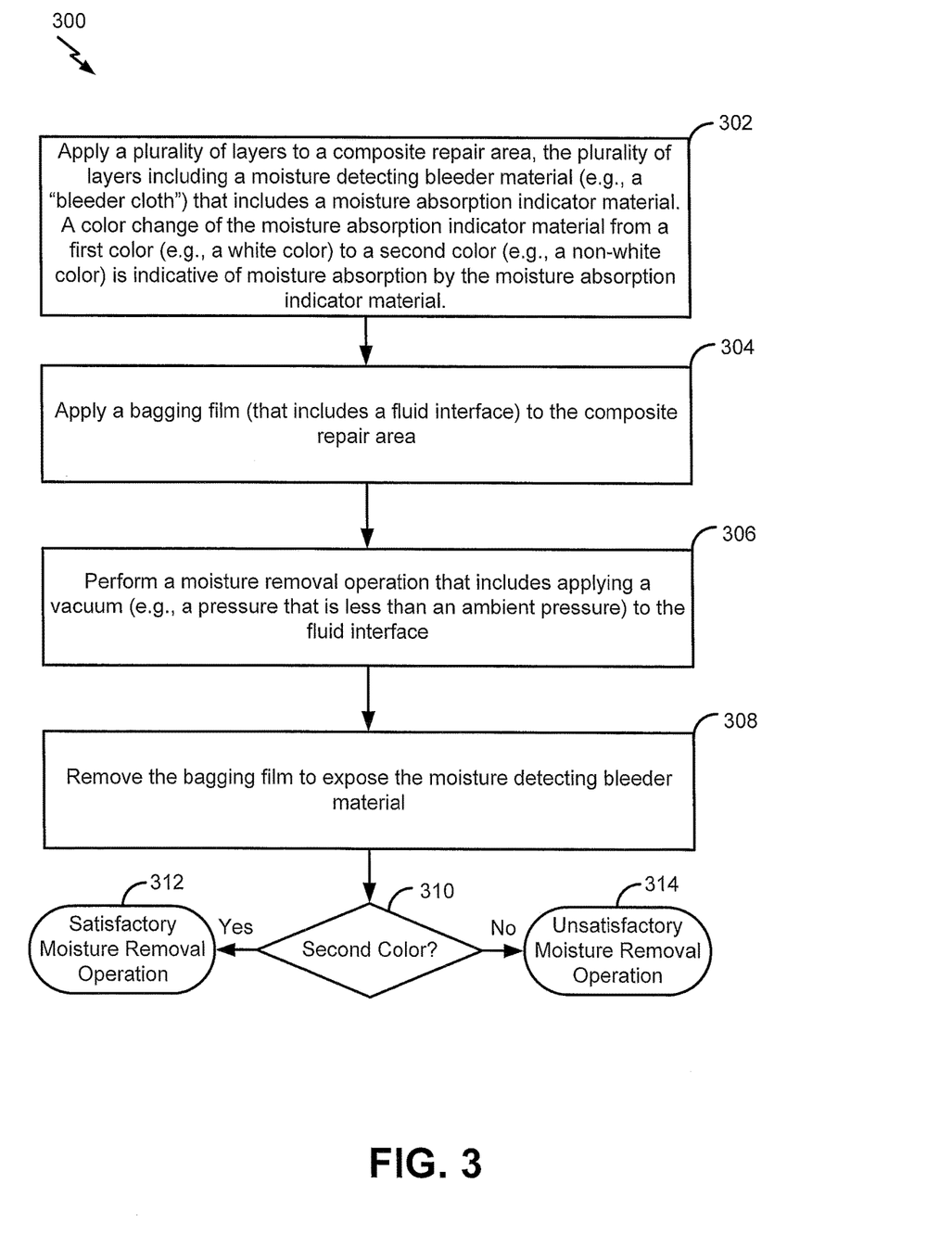
FIG. 3 is a flow chart illustrating a particular embodiment of a method of evaluating a moisture removal operation (associated with a composite repair operation) using a moisture detecting bleeder material.

FIG. 3 illustrates a particular embodiment of a method 300 of evaluating a moisture removal operation using a moisture detecting bleeder material. The moisture detecting bleeder material includes a moisture absorption indicator material, and a color change of the moisture absorption indicator material from a first color to a second color is indicative of moisture absorption by the moisture absorption indicator material. The color change may be indicative of a satisfactory moisture removal operation.

The method 300 includes applying a plurality of layers to a composite repair area, at 302. The plurality of layers includes a moisture detecting bleeder material that includes a moisture absorption indicator material. A color change of the moisture absorption indicator material from a first color (e.g., a white color) to a second color (e.g., a non-white color, such as a blue color) is indicative of moisture absorption by the moisture absorption indicator material. As further described herein, in some cases, the plurality of layers may further include a porous release film layer between the moisture detecting bleeder material and the composite repair area, a heat blanket layer overlying the moisture detecting bleeder material, and a breather layer overlying the heat blanket layer. As described further herein, in some cases, the heat blanket layer 110 may represent a heat source for the moisture removal operation. In other cases, the heat source may be an oven or an autoclave, and the heat blanket layer 110 may be omitted from the plurality of layers. For example, referring to FIG. 1, a plurality of layers including the moisture detecting bleeder material 102 may be applied to the composite repair area 104. FIG. 1 further illustrates an example in which the plurality of layers also includes the porous release film layer 108, the heat blanket layer 110, and the breather layer 112.

The method 300 includes applying a bagging film to the composite repair area, at 304. The bagging film includes a fluid interface to enable application of a vacuum (e.g., a pressure that is less than an ambient pressure) to the composite repair area during a moisture removal operation. For example, referring to FIG. 1, the bagging film 114 may be applied to the composite repair area 104. As shown in FIG. 1, the bagging film 114 includes the fluid interface 116 (illustrated as "Vacuum Out") to provide the moisture path 118 for removal of moisture from the composite repair area 104 during a moisture removal operation of a composite repair operation.

The method 300 includes performing a moisture removal operation that includes applying a vacuum to the fluid interface, at 306. For example, referring to FIG. 1, after sealing the bagging film 114 to the composite part 106 (e.g., using the sealant tape 122), a vacuum (e.g., a pressure that is less than an ambient pressure) may be applied to the fluid interface 116.

The method 300 includes removing the bagging film to expose the moisture detecting bleeder material, at 308. For example, referring to FIG. 1, after performing the moisture removal operation, the bagging film 114 may be removed to expose the moisture detecting bleeder material 102.

The method 300 includes evaluating the exposed moisture detecting bleeder material to determine whether color change occurred, at 310. When the moisture absorption indicator material changes color from the first color to the second color (indicative of moisture absorption by the moisture indicating material), the moisture removal operation may be considered a satisfactory moisture removal operation, as shown at 312. When the moisture absorption indicator material does not change color from the first color to the second color, the moisture removal operation may be considered an unsatisfactory moisture removal operation, as shown at 314.

Thus, FIG. 3 illustrates a particular example of a method of evaluating a moisture removal operation using a moisture detecting bleeder material. The moisture detecting bleeder material includes a moisture absorption indicator material, and a color change of the moisture absorption indicator material from a first color to a second color is indicative of moisture absorption by the moisture absorption indicator material. The moisture detecting bleeder material may be examined after the moisture removal operation in order to determine whether the color change occurred. A color change may be indicative of a satisfactory moisture removal operation.

Figure 4:
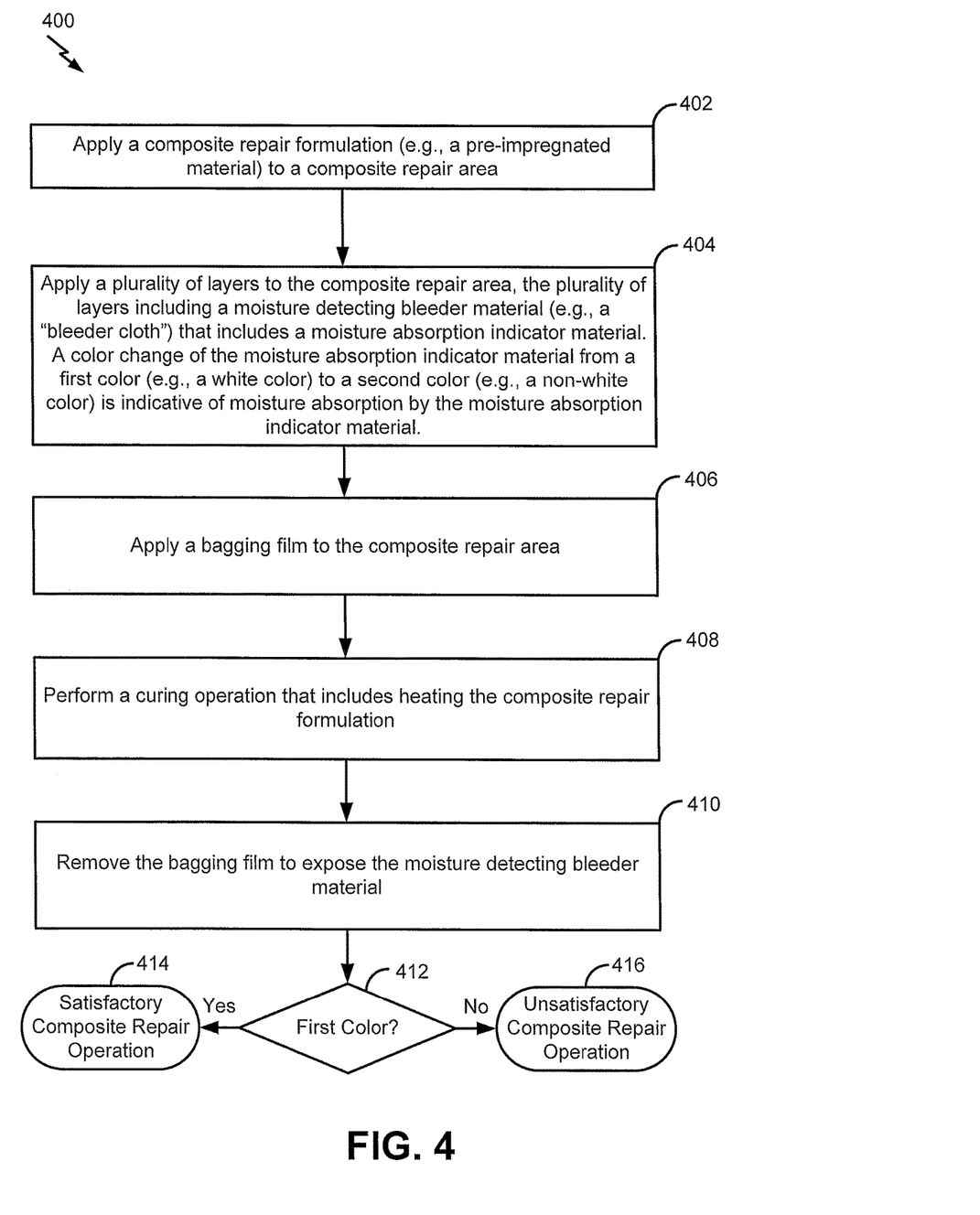
FIG. 4 is a flow chart illustrating a particular embodiment of a method of evaluating a curing operation (associated with a composite repair operation) using a moisture detecting bleeder material.

FIG. 4 illustrates a particular embodiment of a method 400 of evaluating a curing operation using a moisture detecting bleeder material. The moisture detecting bleeder material includes a moisture absorption indicator material, and a color change of the moisture absorption indicator material from a first color (e.g., a white color) to a second color (e.g., a non-white color, such as a blue color) is indicative of moisture absorption by the moisture absorption indicator material. The color change may be indicative of an unsatisfactory curing operation.

The method 400 includes applying a composite repair formulation to a composite repair area, at 402. For example, referring to FIG. 2, the composite repair formulation 202 may be applied to the composite repair area 104.

The method 400 includes applying a plurality of layers to the composite repair area, at 404. The plurality of layers includes a moisture detecting bleeder material that includes a moisture absorption indicator material. A color change of the moisture absorption indicator material from a first color to a second color is indicative of moisture absorption by the moisture absorption indicator material. As further described herein, in some cases, the plurality of layers may further include a porous release film layer between the moisture detecting bleeder material and the composite repair area, a solid release film layer overlying the moisture detecting bleeder material, a heat blanket layer overlying the solid release film layer, and a breather layer overlying the heat blanker layer. As described further herein, in some cases, the heat blanket layer 110 may represent a heat source for the curing operation. In other cases, the heat source may be an oven or an autoclave, and the heat blanket layer 110 may be omitted from the plurality of layers. For example, referring to FIG. 2, a plurality of layers including the moisture detecting bleeder material 102 may be applied to the composite repair area 104. FIG. 2 further illustrates an example in which the plurality of layers also includes the porous release film layer 108 (overlying the composite repair formulation 202 applied to the composite repair area 104), the solid release film layer 204, the heat blanket layer 110, and the breather layer 112. In other cases, the plurality of layers may include fewer layers or more layers.

The method 400 includes applying a bagging film to the composite repair area, at 406. For example, referring to FIG. 2, the bagging film 114 may be applied to the composite repair area 104. As shown in FIG. 2, the bagging film 114 includes the fluid interface 116 (illustrated as "Vacuum Out") to provide the moisture path 118 for removal of moisture in the case of moisture ingression into the composite part 106 and/or moisture ingression as a result of a bagging leak.

The method 400 includes performing a curing operation that includes heating the composite repair formulation, at 408. For example, referring to FIG. 2, a curing operation may be performed that includes heating the composite repair formulation 202 (e.g., via application of heat using the heat blanket layer 110). While not shown in the example of FIG. 2, in other cases, heat may be applied via an oven or an autoclave, and the heat blanket layer 110 may be omitted from the plurality of layers.

The method 400 includes, after curing the composite repair formulation, removing the bagging film to expose the moisture detecting bleeder material, at 410. For example, referring to FIG. 2, the bagging film 114 may be removed to expose the moisture detecting bleeder material 102.

The method 400 includes evaluating the exposed moisture detecting bleeder material to determine whether a color change occurred, at 412. When the moisture absorption indicator material does not change color to the second color (indicative of no moisture incursion during the curing operation), the curing operation may be considered a satisfactory composite repair operation, as shown at 414. When the moisture absorption indicator material changes color to the second color (indicative of moisture incursion during the curing operation), the curing operation may be considered an unsatisfactory composite repair operation, as shown at 416.

Thus, FIG. 4 illustrates a particular example of a method of evaluating a curing operation using a moisture detecting bleeder material. The moisture detecting bleeder material includes a moisture absorption indicator material, and a color change of the moisture absorption indicator material from a first color to a second color is indicative of moisture absorption by the moisture absorption indicator material. The color change may be indicative of the presence of moisture during the curing operation (e.g., resulting from moisture ingression into the composite part, a bagging leak, etc.), representing an unsatisfactory curing operation.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it is to be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A method comprising:
    applying a plurality of layers to a composite repair area, the plurality of layers including a moisture detecting bleeder material that includes a moisture absorption indicator material, wherein an area of the moisture absorption indicator material is larger than or coextensive with the composite repair area, and wherein a color change of the moisture absorption indicator material from a first color to a second color is indicative of moisture absorption by the moisture absorption indicator material;
    applying a bagging film to the composite repair area, the bagging film including a fluid interface;
    performing a moisture removal operation that includes applying a pressure that is less than an ambient pressure to the fluid interface;
    removing the bagging film to expose the moisture detecting bleeder material; and
    evaluating the moisture detecting bleeder material to determine whether the color change occurred.

2. The method of claim 1, wherein the moisture detecting bleeder material includes a bleeder cloth, a bleeder mat, or a combination thereof.

3. The method of claim 1, wherein the plurality of layers includes a porous release film layer in contact with the moisture detecting bleeder material.

4. The method of claim 1, wherein the plurality of layers further includes:
    a porous release film layer between the moisture detecting bleeder material and the composite repair area; and
    a breather layer overlying the moisture detecting bleeder material.

5. The method of claim 1, wherein the color change is thermally irreversible below a temperature of 450° F.

6. The method of claim 1, wherein the moisture absorption indicator material includes a metal halide material.

7. The method of claim 6, wherein the metal halide material is a component of a silica gel.

8. The method of claim 6, wherein the metal halide material includes a chloride material, a bromide material, or a combination thereof.

9. The method of claim 6, wherein the metal halide material includes nickel, cobalt, or a combination thereof.

10. The method of claim 1, further comprising after determining that the color change occurred:
    applying a composite repair formulation to the composite repair area;
    after applying the composite repair formulation, applying the plurality of layers to the composite repair area;
    applying the bagging film to the composite repair area;
    performing a curing operation that includes heating the composite repair formulation;
    removing the bagging film to expose the moisture detecting bleeder material; and
    evaluating the moisture detecting bleeder material to determine whether the color change occurred.

11. The method of claim 10, further comprising determining that moisture incursion occurred during the curing operation when the color change occurred.

12. The method of claim 10, wherein the composite repair formulation includes one or more volatile components, and wherein exposure of the moisture absorbing indicator material to the one or more volatile components does not result in the color change from the first color to the second color.

13. The method of claim 10, wherein the plurality of layers further includes:
    a porous release film layer between the moisture detecting bleeder material and the composite repair area;
    a solid release film layer, wherein the moisture detecting bleeder material is between the porous release film layer and the solid release film layer; and
    a breather layer overlying the solid release film layer.

14. The method of claim 10, wherein the color change is thermally irreversible below a threshold temperature of 450° F., and wherein the composite repair formulation is heated to a curing temperature that does not exceed the threshold temperature.

15. A method comprising:
    applying a composite repair formulation to a composite repair area;
    after applying the composite repair formulation, applying a plurality of layers to the composite repair area, the plurality of layers including a moisture detecting bleeder material that includes a moisture absorption indicator material and a porous release film layer between the moisture detecting bleeder material and the composite repair area, wherein the porous release film layer is directly coupled to the moisture detecting bleeder material, and wherein a color change of the moisture absorption indicator material from a first color to a second color is indicative of moisture absorption by the moisture absorption indicator material;
    applying a bagging film to the composite repair area;
    performing a curing operation that includes heating the composite repair formulation;
    removing the bagging film to expose the moisture detecting bleeder material; and
    evaluating the moisture detecting bleeder material to determine whether the color change occurred.

* * * * *